(12) United States Patent
Shang

(10) Patent No.: US 10,987,520 B2
(45) Date of Patent: Apr. 27, 2021

(54) VASCULAR OPTICAL FIBER GUIDEWIRE

(71) Applicant: Hua Shang, Nanjing (CN)

(72) Inventor: Hua Shang, Nanjing (CN)

( * ) Notice: Subject to any disclaimer, the term of this patent is extended or adjusted under 35 U.S.C. 154(b) by 0 days.

(21) Appl. No.: 16/853,507

(22) Filed: Apr. 20, 2020

(65) Prior Publication Data

US 2021/0060349 A1 Mar. 4, 2021

Related U.S. Application Data

(63) Continuation of application No. PCT/CN2019/105112, filed on Sep. 10, 2019.

(30) Foreign Application Priority Data

Aug. 9, 2019 (CN) .......................... 201910735040.3

(51) Int. Cl.
| | |
|---|---|
| *A61N 5/06* | (2006.01) |
| *G02B 6/44* | (2006.01) |
| *A61M 25/09* | (2006.01) |
| *A61N 5/067* | (2006.01) |

(52) U.S. Cl.
CPC .......... *A61N 5/0601* (2013.01); *A61M 25/09* (2013.01); *G02B 6/4415* (2013.01); *A61M 2025/09075* (2013.01); *A61M 2205/0238* (2013.01); *A61M 2205/0266* (2013.01); *A61N 2005/063* (2013.01); *A61N 2005/067* (2013.01)

(58) Field of Classification Search
None
See application file for complete search history.

(56) References Cited

U.S. PATENT DOCUMENTS

| | | | |
|---|---|---|---|
| 4,986,628 A | 1/1991 | Lozhenko et al. | |
| 5,196,005 A | 3/1993 | Doiron et al. | |
| 5,207,669 A | 5/1993 | Baker et al. | |
| 5,269,777 A | 12/1993 | Doiron et al. | |
| 5,330,465 A | 7/1994 | Doiron et al. | |
| 6,398,778 B1 | 6/2002 | Gu et al. | |
| 2010/0274235 A1* | 10/2010 | Mihajlovic | A61B 5/0084 606/15 |
| 2019/0133687 A1* | 5/2019 | Eshkol | G02B 6/036 |

* cited by examiner

*Primary Examiner* — Brian T Gedeon
(74) *Attorney, Agent, or Firm* — Andrew D. Fortney; Central California IP Group, P.C.

(57) ABSTRACT

Disclosed is a novel vascular optical fiber guidewire. The vascular optical fiber guidewire includes a metal axial wire and an optical fiber surrounding the metal axial wire. The optical fiber includes a core wire and a cladding layer covering the core wire. For above vascular optical fiber guidewire, in a part of the optical guidewire that is required to transmit light, a bending radius of the optical fiber around the metal axial wire is greater than a critical bending radius, and in a region of the optical fiber guidewire that is required to scatter light, the bending radius of the optical fiber around the metal axial wire is less than the critical bending radius. The present disclosure is capable of entering a blood vessel by a percutaneous puncture technique, guiding the optical fiber guidewire through a medical imaging device in a blood vessel, and performing side-illumination on the head.

20 Claims, 7 Drawing Sheets

VASCULAR OPTICAL FIBER GUIDEWIRE

CROSS-REFERENCE TO RELATED APPLICATIONS

This application is a continuation of PCTCN2019/105112, filed on Sep. 10, 2019, pending, which claims priority to Chinese Patent Application No. 201910735040.3, filed on Aug. 9, 2019, the entireties of which are both incorporated herein by reference.

TECHNICAL FIELD

The present disclosure belongs to technical fields of medical and optical, relates to a novel vascular optic fiber guidewire, and specifically to a side-illuminated vascular optical fiber guidewire.

BACKGROUND

At present, Seldinger arterial intubation technique is very mature. Under the guidance of clinical imaging medicine (X-ray, CT, MR, B-us, etc.), a delicate instrument, such as a special catheter or guidewire is inserted into the lesion via percutaneous vascular route or an original channel in human body, so as to achieve a diagnostic imaging and treatment. This technique uses a metal guidewire via percutaneous vascular route to enter blood vessels and reach the lesion. This method is simple in operation, slight in damage, and does not need to suture the blood vessels. Thus, it completely replaces previous methods which need to cut open the blood vessels surgically, and becomes a basic operation technique of modem interventional radiology. This method has achieved good effects in tumor thrombosis and drug perfusion, intra-arterial irradiation, prevention of radiation damage, chemotherapy, preoperative embolization of tumor blood vessels, vasoactive drugs and alcohol perfusion, etc. However, due to the limitation of the treatment mode, the existing treatment mainly relies on the embolization to cause tissue ischemia, hypoxia and necrosis, or perfusion of drugs to inhibit cell growth, or the release of implanted medical devices to change the shape of organs and tissues, and thus it is impossible to introduce light into blood vessels and body or to lead light out blood vessels and body.

Compared with conventional treatments such as surgery, chemotherapy and radiotherapy, photodynamic therapy of tumor has several advantages, such as small trauma, low toxicity, good targeting and good applicability. However, irradiation means is limited to the body surface or big channels, depending on the laser emission mechanism and pharmacological properties of photosensitizer. In such situation, the photo-dynamics of photodynamic therapy may work only on the area of a few millimeters, which greatly limits its application in the medical field.

Optical fiber is used in the medical field to guide light from the light source to the lesion site, and is widely used in photodynamic therapy, surgical hemostasis and tumor laser hyperthermia. Since the end face of optical fiber is generally only on the order of a few micrometers to a hundred micrometers, the emitted laser light has a small irradiation area to the tissue, and a homogenizing device is required to uniformly distribute the laser light in the lesion site. In general, the homogenizing device is required to emit light along the side, to have a uniform luminous length of about 5 mm to 50 mm, and to be thin enough to be used in a device such as a puncture needle or an endoscope.

There are a variety of scattering-type side-illuminated and homogenizing device that scatter light out of the side of the optical fiber through scatterers (such as powders, beads, gratings, etc.) in the core wire of the optical fiber. For example, U.S. Pat. Nos. 5,196,005 and 5,330,465 disclose that powder scatterers are embed into a silica core layer at the end of the optical fiber, and the concentration of the powder scatterers increases with increasing of length. U.S. Pat. No. 5,269,777 discloses that the powder scatterers are incorporated in the cladding layer of the optical fiber, rather than being doped in the core layer. U.S. Pat. No. 4,986,628 describes a method of incorporating a scatterer into a polymer. U.S. Pat. No. 6,398,778 B1 uses a fiber grating arranged in an optical fiber to scatter light, in which the fiber grating is a type II Bragg grating, and the refractive index is modulated by the grating to laterally scatter the light along the optical fiber. U.S. Pat. No. 5,207,669 proposes the out cladding layer of the multimode fiber is constructed by gradually thinning along the length of the fiber, wherein due to the thinning of the outer cladding layer, part of the light transmitted in the core wire is exited from the side of the optical fiber by means of evanescent waves, and the remainder continues to be transmitted in the core layer up to out of the fiber.

All of the above methods for forming a beam homogenizing device have some disadvantages: the production of special doping scatterers and graded fiber gratings requires a high processing process, which inevitably leads to an increase in cost; part of the scatterer structure is prone to breakage caused by heat absorption when the light intensity is strong, thereby destroying the function of the homogenizer, these scatterers are generally large in diameter, and cannot be guided through the blood vessels of the human body and guided through the catheter.

SUMMARY

An object of the present disclosure is to provide a novel vascular optical fiber guidewire. The novel vascular optical fiber guidewire is capable of entering blood vessels by a percutaneous puncture technique, guiding in blood vessels through a medical imaging, and performing side illumination on the head.

The present disclosure provides a side-illuminated vascular optical fiber guidewire, including a light-conducting portion and a light-emitting portion, and the light-conducting portion and the light-emitting portion are connected to each other.

The light-emitting portion includes a metal axial wire and an optical fiber surrounding the metal axial wire. The optical fiber includes a core wire and a cladding layer covering the core wire.

In the above mentioned vascular optical fiber guidewire, the light-emitting portion is located at a distance of 50 mm from a top end of optical fiber guidewire.

In the light-emitting portion, when a bending radius of the optical fiber around the metal axial wire is less than a critical bending radius, the cladding layer is unable to restrain the light transmitted in the core wire, causing a light to leak from the side wall by passing through the cladding layer; if the bending radius of the optical fiber around the metal axial wire is greater than the critical bending radius, the light is transmitted in the core wire and may not pass through the cladding layer and leak out from the side wall of the cladding layer.

In a specific example of the present disclosure, a length of the light-conducting portion of the optical fiber guidewire is 1.6 m, and a side-illuminated structure, i.e., the light-emitted portion, is located at a distance of 50 mm from the top end.

In the disclosure, the optical fiber is a light-conducting device that restrains the transmission of light in the core wire by comparing a refractive index of the core wire with that of the cladding layer.

The bending radius R of the optical fiber includes a value of the critical bending radius Rc. The critical bending radius Rc is a minimum radius at which the cladding layer may directly restrains the light transmitted in the core wire, resulting in light not leaking from the side wall. Specifically, in the light-emitting portion of the optical fiber guidewire, when the optical fiber has a large spiral pitch such that the bending radius is much larger than Rc, light is confined to be transmitted inside the cladding layer; in a region where light is required to be scattered, such as in a head portion (i.e., the light-emitting portion) of the optical fiber guidewire, the pitch surrounded by the optical fiber is reduced and the bending radius R of the optical fiber is reduced to be smaller than Rc, the light will leak from the cladding layer and scatter into the surrounding environment through the side face. The pitch of the optical fiber around the metal axial wire is a variable. When this variable has a suitable value as function of the radial change of the axial wire, the light scattered from the side face will have a constant intensity to achieve a uniform side-illumination.

In the above vascular optical fiber guidewire, the bending loss of the transmission power of the optical fiber due to the bending around the metal axial wire is an optical power of the light emitted from the bending side.

The relationship between the bending loss of a single-mode fiber and the bending radius of the optical fiber is calculated according to formula I:

$$\alpha_c = A_c R^{-1/2} \exp(-UR) \qquad \text{formula I}$$

where $$A_c = \frac{1}{2}\left(\frac{\pi}{a}\right)^{1/2} 3.7\left(\frac{\lambda_c}{\lambda}\right)^2 \qquad \text{formula I-1}$$

$$U \approx 0.705 \frac{\Delta n^{3/2}}{\lambda}\left(2.748 - 0.996 \frac{\lambda}{\lambda_c}\right)^3 \qquad \text{formula I-2}$$

In the formula I, the formula I-1, the formula I-2, $\alpha_c$ represents the power loss per unit length of the single-mode fiber in dB; R represents the bending radius of the optical fiber in mm; $A_c$ represents the parameters related to the optical fiber structure in dB/m½; a represents the radius of core wire of the optical fiber in μm; $\lambda_c$ represents the cutoff wavelength of the optical fiber transmission in nm; $\Delta n$ represents the refractive index difference between the core wire and the cladding layer.

In the formula I-1, $$k_0 = \frac{2\pi}{\lambda},$$

$k_0$ is the vacuum wave number, where $\lambda$ represents the transmission wavelength of the optical fiber;

$$\lambda_c = \frac{2\pi a}{V_c}\sqrt{n_1^2 - n_2^2},$$

where $n_1$ and $n_2$ respectively represent the refractive index of the core wire and cladding layer of the optical fiber; $V_c$ represents the cutoff frequency and $V_c$=2.40483.

In the above vascular optical fiber guidewire, the bending radius of the optical fiber is related to the angle between the spiral line of the optical fiber and the side line of the cylinder that is formed by winding the spiral line with radius r, and is calculated according to formula II:

$$R = \frac{4\pi^2 r^2 + (2\pi r \cdot \cot(\theta))^2}{4\pi^2 r}. \qquad \text{formula II}$$

In formula II, R represents the bending radius of the optical fiber, θ represents the angle between the spiral line and the side line of the cylinder, and r represents the spiral winding radius of the optical fiber.

The relationship between a longitudinal length of the optical fiber and the angle between the spiral line of the optical fiber and the spiral line of the optical fiber and the side line of the cylinder that is formed by winding the spiral line with radius r is calculated according to formula III:

$$-\frac{\ln(10)}{10}\alpha_c(\theta(z)) \cdot \cos(\theta(z)) \cdot (-s_0 \cdot z + s_1) = -s_0. \qquad \text{formula III}$$

In formula III, z represents the longitudinal length of the optical fiber along the metal axis, θ represents the angle between the spiral line and the side line of the cylinder; $\alpha_c$ represents the power loss per unit length of the single-mode optical fiber in dB; $s_1$ represents the initial power, $s_0$ represents the rate of power attenuation.

In the above vascular optical fiber guidewire, when bringing θ(z) obtained from formula III into the following formula IV, the optical power exited from the side face of the optical fiber may be calculated:

$$P(z) = \frac{s_0}{\frac{\ln(10)}{10}\alpha_c(\theta(z)) \cdot \cos(\theta(z))} \qquad \text{formula IV}$$

P(z) represents the optical power exited from the side face of the optical fiber, i.e., the distribution of the optical power on the longitudinal length of the fiber along the metal axis; z represents the longitudinal length of the fiber along the metal axis: θ represents the angle between the spiral line and the side line of the cylinder: $\alpha_c$ represents the power loss per unit length of a single-mode fiber in dB.

In the above-mentioned vascular optical fiber guidewire, the pitch of the optical fiber to be set may be calculated by bringing the angle between the spiral line and the side line of the cylinder obtained from formula II or formula III into formula V:

$$h = 2\pi r \cdot \cot(\theta) \qquad \text{Formula V.}$$

In formula V, h represents the pitch of the optical fiber, r represents the spiral winding radius of the optical fiber, and θ represents the angle between the spiral line and the side line of the cylinder.

In the above vascular optical fiber guidewire, a diameter of the metal axial wire may be 50 μm to 1 mm.

In order to increase the winding tightness of the optical fiber, a spiral groove may be provided on the metal axial wire, so as to embed the optical fiber in the spiral groove.

In the above vascular optical fiber guidewire, in order to increase the flexibility of the metal axial wire, a hole-like structure may be provided on the metal axial wire 2 to lower the hardness of the metal axial wire.

A polymer sleeve may be arranged outside the optical fiber guidewire, so as to increase the stability and safety of the overall structure.

In the disclosure, a material of the polymer sleeve is at least one selected from polyethylene, polyvinyl chloride, epoxy resin, aliphatic polyester, chitin and polylactic acid.

In the above vascular optical fiber guidewire, the metal axial wire is provided with a longitudinal spiral groove on a side opposite to the spiral groove, to reduce the hardness of the metal axial wire.

A hydrophilic and/or hydrophobic coating is arranged outside the polymer sleeve, so as to reduce resistance of the vascular optical fiber guide wire in the blood and increases biocompatibility.

In the above vascular optical fiber guidewire, a material of the optical fiber is at least one selected from a quartz optical fiber, a polymer optical fiber or a glass optical fiber.

A material of the metal axial wire is at least one selected from stainless steel, aluminum alloy, titanium alloy or nickel titanium alloy, and may also be carbon fiber, polymer material or the like.

In the disclosure, the polymer material used in the metal axial wire is at least one selected from polyethylene, polyvinyl chloride, epoxy resin, aliphatic polyester, chitin and polylactic acid.

In the disclosure, one end of the light-conducting portion is connected with the light-emitted portion, and other end of the light-conducting portion is connected with a plug capable of connecting with a laser other optical fiber, preferably a memory apply plug.

The present disclosure has the following advantages.

1. The pitch of the optical fiber around the metal axial wire is a variable. When this variable has a suitable value as function of the radical change of the axial fiber z, the light scattered from the side face will have a constant intensity to achieve a uniform side-illumination.

2. In the main light-conducting portion of the optical fiber guide wire, it is not necessary to leak light from the cladding layer, and thus the pitch is set to a value much larger than the critical bending radius Rc; and in the top of the optical fiber guide wire, such as at where from the top 50 mm, the pitch is set to gradually decrease, and the value is changed according to the relationship shown in FIG. 4, and thus the light with a constant intensity will scatter from the top along the side face.

3. The arrangement of the spiral groove may increase the winding tightness of the optical fiber.

4. The arrangement of the hole-like structure may increase the flexibility of the metal axial wire.

5. The arrangement of the longitudinal spiral groove may reduce the hardness of the metal axial wire.

6. The polymer sleeve may increase the stability and safety of the overall structure; the arrangement of the hydrophilic and/or hydrophobic coating outside the polymer sleeve may reduce resistance of the vascular optical fiber guide wire in the blood and increase biocompatibility.

7. The vascular fiber guide wire of the present disclosures realizes the connection of the optical fiber guidewire with the laser or other devices through the memory alloy plug. Therefore, the vascular fiber guide wire may be extended to achieve in vivo treatment, or connected with a laser or the like to introduce laser into the vascular fiber guidewire for treatment. When the memory alloy plug is connected with other jack sets, the insertion and extraction operations are convenient. In addition, the optical fiber is rotatable after inserting the plug, so the coupling efficiency would not be affected.

Figure 1:
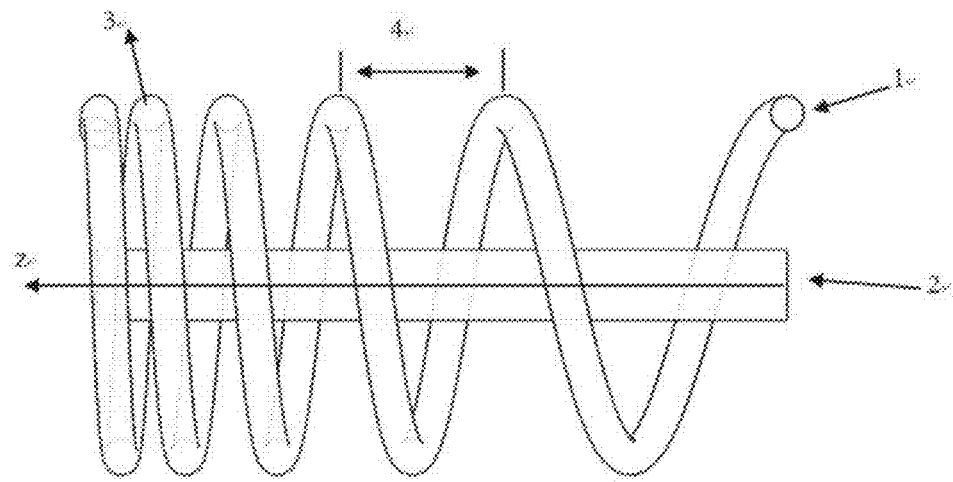
FIG. 1 is a schematic diagram illustrating the structure of a side-illuminated vascular optical fiber guidewire.

LIST OF REFERENCE NUMERALS 1, optical fiber; 2, metal axial wire; 3, light scattering point: 4, pitch; 5, spiral groove; 6, hole; 7, structural spiral groove; 8, polymer and/or hydrophobic coating; 9, elastic deformable spiral structure: 10, main body; 11, elastic pin; 12, cavity: 13, rolling ring; 14, connecting optical fiber; 16, opening; 20, light-emitting portion; 21, light conducting portion; 22, memory alloy plug; 23, optical fiber core wire: 24, optical fiber cladding layer; 25, metal tube; 26, polymer coating; 27, handle; 28, fixing groove; 29, sleeve; 30, spiral tube; 110, connecting portion; 111, elastic portion; 112, fixing portion; 210, conducting optical fiber.

DETAILED DESCRIPTION

The experimental methods used in the following examples are conventional methods unless otherwise specified.

The materials, reagents and the like used in the following examples are commercially available unless otherwise specified.

Example 1

As shown in FIG. 1, it is a basic principle structure diagram of the present disclosure. The side-illuminated vascular fiber guide wire of the present disclosure includes a light-conducting portion for transporting laser: one end of the light-conducting portion (i.e., the end that enters the human body) is connected with a light-emitting portion capable of emitting light. There are many means, such as welding, integral molding, removable connection and any other conventional connection methods in the art, which can be used for connecting the light-emitting portion and the light-conducting portion. In addition, the optical fiber of the light-conducting portion is paired with the optical fiber of the light-emitting portion to transmit all of the light to the optical fiber of the light-emitting portion. The optical fibers are preferably integrally formed, so as to achieve high light transmission efficiency, which may be determined according to actual conditions.

The light-emitting portion includes a metal axial wire 2 and an optical fiber 1 surrounding the metal axial wire. The optical fiber 1 includes a core wire and a cladding layer covering the core wire. The optical conductivity of the cladding layer is smaller than that of the core wire. In normal circumstances, light can only be transmitted from the core wire and cannot be scattered from the cladding layer. This is a kind of light-conducting device that restrains the transmission of light in the core wire by comparing a refractive index of the core wire with that of the cladding layer (e.g., the refractive index of the core wire is 1.5, and the refractive index of the cladding layer is 1.3).

In the light-emitting portion, if a bending radius of the optical fiber 1 around the metal axial wire is less than a critical bending radius, the cladding layer will be unable to restrain the light transmitted in the core wire, causing light to leak from the sidewall by passing through the cladding layer, and this phenomenon is called as a side-illumination; if the bending radius of the optical fiber around the metal axial wire is greater than the critical bending radius, the light is only transmitted in the core wire, and cannot pass through the cladding layer and leak from the side wall. In practical applications, when the optical fiber of the light-emitting portion is spirally wound around the periphery of the metal axial wire, it may have different bending radiuses at different positions. For example, the bending radius is smaller than the critical bending radius at where the side-illumination is required; and the bending radius is greater than the critical bending radius at where the side-illumination is not required. Of course, it is also possible to exit light at various positions of the optical fiber as needed, or even every positions of the optical fiber.

A length of the light-conducting portion may be 0.1 m to 2 m, such as 1.6 m, and a length of the light-emitting portion may be 10 mm to 100 mm, such as 50 mm, depending on actual requirements.

In this example, the bending radius R of the optical fiber includes a value of the critical bending radius Rc. The critical bending radius Rc is a minimum radius at which the cladding layer can directly restrains the light transmitted in the core wire, resulting in light not leaking from the side face. Specifically, in the light-emitting portion, when the pitch surrounding by the optical fiber is reduced and the bending radius R of the optical fiber is smaller than Rc, light will leak from the cladding layer and scatter into the surrounding environment through the sidewall. The pitch of the optical fiber around the metal fiber is a variable. When this variable has a suitable value as function of the radical change of the axial fiber, the light scattered from the side face will have a constant intensity to achieve a uniform side-illumination.

In this example, a bending loss at the bend of the optical fiber is the optical power of the light exited from the bending side face, and the relationship between the bending loss and the bending radius of the optical fiber is as shown in formula I of the Summary.

The bending radius of the optical fiber is related to the angle between the spiral line of the optical fiber and the side line of the cylinder that is formed by winding the spiral line with radius r, and is calculated according to formula II.

The relationship between the longitudinal length of the winding of the optical fiber and the angle between the spiral line of the optical fiber and the side line of the cylinder that is formed by winding the spiral line with radius r is calculated according to formula III.

The optical power exited from the side face of the optical fiber is calculated according to formula IV.

The specific formulas I-IV are as mentioned in the Summary. Through the above formulas, the characteristic of the emitted light (such as optical power, bending loss), bending radius and so on can be calculated through different parameters. The corresponding formula can be selected according to the parameters that need to be obtained or calculated, which is convenient and quick.

In addition, in this example, the light-emitting portion can be set to emit light only on one side. That is, when the optical fiber 1 is located on the light-emitting side of the light-emitting portion and the bending radius thereof is smaller than the critical bending radius, light-emitting positions at each spiral coil will be connected together to form a line parallel to the axis z of the optical fiber guidewire, which is equivalent to distributing the light-emitting positions along the axis z of the optical fiber guidewire. Referring to FIG. 1, the light-emitting positions are all located at the top of each spiral, i.e., the position indicated by light scattering point 3. In practical applications, it is usually arranged to emit light along the axis z on one or both sides of the optical fiber guidewire.

In this example, the structure of the light-conducting portion of optical fiber guidewire includes, but is not limited to, any one of i) to v). i) Like the structure of the light-emitting portion, the conducting portion includes a metal axial wire of the conducting portion and an optical fiber of conducting portion surrounding the metal axial wire of the conducting portion. The conducting portion also includes an optical core wire of the conducting portion and an optical fiber cladding layer wrapped around the periphery of the optical core wire. The bending radius of the optical fiber of the conducting portion is greater than the critical bending radius, so that the light can only be confined to transmit in the optical core wire and cannot be scattered from the optical fiber cladding layer. The main function of the light-conducting portion is to conduct light. ii) The light-conducting portion only includes the optical fiber of the conducting portion. The optical fiber of the conducting portion includes an optical core wire and an optical fiber cladding layer wrapped around the periphery of the core wire. The light can only be transmitted in the optical core wire and scattered from the end face, and cannot be emitted from the side face. iii) The light-conducting portion includes the optical fiber of the conducting portion and a polymer layer or metal layer wrapped around the optical fiber wire. iv) The light-conducting portion includes an optical fiber of the conducting portion and a metal wire spirally wound around the fiber of the conducting portion. Of course, a polymer layer may be coated outside the metal wire. v) The optical fiber guide wire may be similar to the optical fiber structures involved in other patents previously filed by the applicant. In order to distinguish it from the terms of the optical fiber, the core wire, the cladding layer and the like of the light-emitting portion, this paragraph uses the term optical fiber of the conducting portion, the optical core wire, and the optical fiber cladding layer to define the optical fiber structure of the light-conducting portion, to avoid confusion.

Example 2

Figure 2:
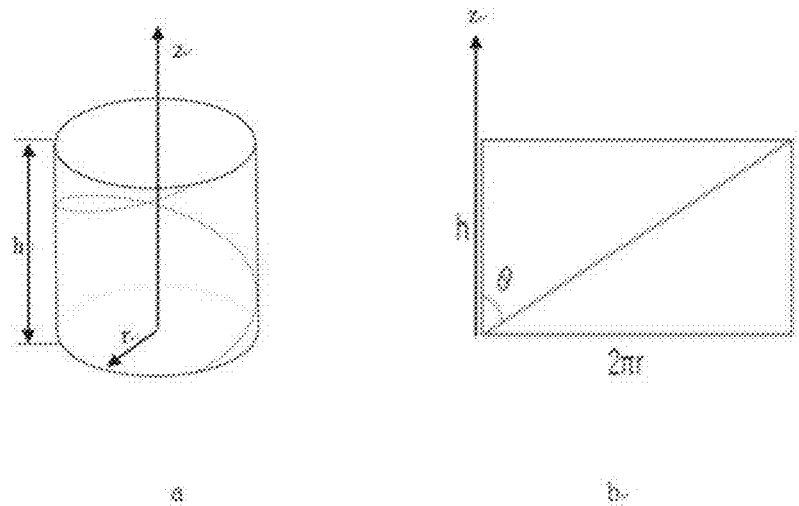
FIG. 2 is a schematic diagram illustrating the expansion of spiral structure according to the side surface of cylinder.

On the basis of example 1, when the optical fiber 1 is bent, if the bending radius of the bending portion is less than Rc (critical bending radius is a minimum radius at which the cladding layer can directly restrains the light transmitted in the core wire, resulting in light not leaking from the side face), the cladding layer will be unable to restrain the light transmitted in the core wire, causing light to leak from the side face. The present disclosure utilizes the principle to construct a structure that the metal axial wire is around by the optical fiber. In the part where the optical fiber guidewire is used to transmit light, i.e., the part where a side-illumination is not required, the rotating pitch of the optical fiber is large, and thus the bending radius thereof will be much larger than Rc. Therefore, light cannot be exited from the cladding layer and is restrained to transmit inside the cladding layer. In the region where light is required to be scattered, such as the head portion of the optical fiber guidewire, the pitch of the optical fiber is reduced and the bending radius of the fiber is reduced to less than Rc, light will leak from the cladding layer and scatter into the surrounding environment. The pitch of the optical fiber around the metal axial wire is a variable. When this variable has a suitable value as function of the radical change of the axial fiber z (See FIG. 2), the light scattered from the side face will have a constant intensity to achieve a uniform side-illumination.

The bending of the optical fiber causes the leak of light from the cladding layer. The leak of light reduces the optical power transmitted in the core wire, resulting in bending loss of the transmission power.

The loss per unit length is calculated according to the bending loss of the single-mode fiber formula (1):

$$\alpha_c = A_c R^{-1/2} \exp(-UR) \quad (1)$$

where $$A_c = \frac{1}{2}\left(\frac{\pi}{aW^3}\right)\left[\frac{u}{Wk_1(W)}\right]^2$$

$$U = \frac{4\Delta n W^3}{3aV^2 n_2}$$

a and $\Delta n$ respectively represent the radius of the core wire and the difference of refractive index between the core wire and the cladding layer; u, W and V respectively represent the radial normalized phase constant, radial normalized decay constant and normalized frequency. The formulas are shown as follows:

$$u^2 = a^2(n_1^2 k_0^2 - \beta_z^2)$$
$$W^2 = a^2(\beta_z^2 - n_2^2 k_0^2)$$
$$V = ak_0(n_1 - n_2)^{1/2} \approx ak_0(2n_2\Delta n)^{1/2}$$

where $k_0$ represents vacuum wave number $$k_0 = \frac{2\pi}{\lambda}, \beta_z$$

is the propagation constant in the z direction.

According to the transmission equation of the optical fiber, some characteristic parameters of the optical fiber transmission can be obtained:

Cutoff frequency: $V_c = 2.40483$
Cutoff wavelength:

$$\lambda_c = \frac{2\pi a}{V_c}\sqrt{n_1^2 - n_2^2}$$

V and W are represented by the above characteristic parameters as:

$$V = 2.405\frac{\lambda_c}{\lambda}$$

$$W = 1.1428V - 0.996 \approx 2.7484\frac{\lambda_c}{\lambda} - 0.996.$$

The approximate expression of U in $m^{-1}$ can thus be obtained:

$$U \approx 0.705\frac{\Delta n^{3/2}}{\lambda}\left(2.748 - 0.996\frac{\lambda}{\lambda_C}\right)^3.$$

In addition, $$\frac{W^{-\frac{2}{3}}u^2}{W^2 K_1^2(W)}$$

can be simplified to $$3.7\left(\frac{\lambda_C}{\lambda}\right)^2,$$

and thus $$A_C = \frac{1}{2}\left(\frac{\pi}{a}\right)^{1/2} 3.7\left(\frac{\lambda_C}{\lambda}\right)^2,$$

its unit is $$dB/m^{\frac{1}{2}}.$$

Based on the above, the relationship between the bending loss formula of the single-mode fiber and the bending radius R is obtained.

Assuming that the length of the optical fiber is L, depending on the bending loss, the relationship among the bending loss, the exited power and the incident power is as follows:

$$a_C \cdot L = -10\log\left(\frac{P(L)}{P(0)}\right) = \frac{-10}{\ln(10)}\ln\left(\frac{P(L)}{P(0)}\right).$$

Here, a log of a base-10 logarithm is transformed into the natural logarithm ln. P(0) is the incident optical power and P(L) is the exited optical power. Then, there is shown as below.

$$P(L) = P(0) \cdot \exp\left(-\frac{\ln(10)}{10}\alpha_C \cdot L\right).$$

When $\alpha_c$ changes with the change of the length L due to the change of the pitch, the above formula may be in the differential form:

$$dP(L) = -\frac{\ln(10)}{10}\alpha_C \cdot P(L)dL.$$

In addition, due to the change of pitch, the optical fiber winding length L is no longer in a linear relationship with the longitudinal length z. However, it is required to make the illumination along z as uniform as possible, rather than to obtain uniform illumination along the fiber winding length L. Therefore, it is necessary to transform the relationship between L and z.

As shown in FIG. 2a, the spiral line is wound around a cylinder of radius r, and the pitch is h. If the side surface of the cylinder is expanded into a plane, as shown in FIG. 2b, the angle between the spiral line and the side line of the cylinder will be θ. When this angle θ changes and the pitch of the spiral line changes, the radius of curvature R will also change.

The relationship among the radius of curvature, pitch h and the winding radius r of the spiral line is $$R = \frac{4\pi^2 r^2 + h^2}{4\pi^2 r}.$$

As $h = 2\pi r \cdot \cot(\theta)$, it will be that $$R = \frac{4\pi^2 r^2 + (2\pi r \cdot \cot(\theta))^2}{4\pi^2 r}.$$

Thus, the curvature radius R of the optical fiber, or $\alpha_c$ is only related to the variable angle θ. In addition, L and z have the following relationship:

$$dl = \cos(\theta)dz.$$

Thus, $$dP(z) = \frac{\ln(10)}{10}\alpha_C(\theta(z)) \cdot P(z)\cos(\theta(z))dz \quad (3)$$

Here, both L and θ are ultimately expressed as function of z.

The final result of the power variation in the optical fiber is $$\frac{dP(z)}{dz} = -s_0. \quad (4)$$

Power is linearly attenuated at a constant rate as z increases. The attenuated light exits from the side face of the optical fiber, and the exited optical power is distributed along the length z at a constant rate.

The above formula is integrated to obtain:

$$P(z) = -s_0 \cdot z + s_1.$$

The physical meaning of the above formula is that: at z=0, the initial power is $s_1$, and the rate of power attenuation is $s_0$. The formula (4) in the differential form can be transformed to:

$$dP(z) = -s_0 dz.$$

Compared with the formula (3), the following formula can be obtained:

$$-\frac{\ln(10)}{10}\alpha_C(\theta(z)) \cdot P(z)\cos(\theta(z)) = -s_0. \quad (5)$$

When the expression of P(z) is brought into the formula (5), the below formula can be obtained:

$$-\frac{\ln(10)}{10}\alpha_c(\theta(z)) \cdot \cos(\theta(z)) \cdot (-s_0 \cdot z + s_1) = -s_0. \quad (6)$$

The above formula is the transcendental formula of the implicit function of the θ(z) function with respect to the variable z. The relationship between θ(z) and z can be obtained by numerical solution.

Specifically, the above calculation evolution can be illustrated by the following parameters.

Assuming that the power of the laser at the incident end of the optical fiber is 1 W, i.e., P(0)=1, the power at the exit end is 0 W (i.e., light is totally scattered), the length of the metal axis of the spiral optical fiber is 50 mm (0.05 m), i.e., P(z=0.05)=), it will obtain that $s_0$=20, $s_1$=1.

The single-mode fiber has a core wire radius of 4.5 μm, a cladding layer diameter of 125 μm, the he refractive index of $n_1$=1.445593 and n=1.444687, the radius of the fiber around the cylinder of 200 μm, and the transmission wavelength of 652 nm.

Figure 3:
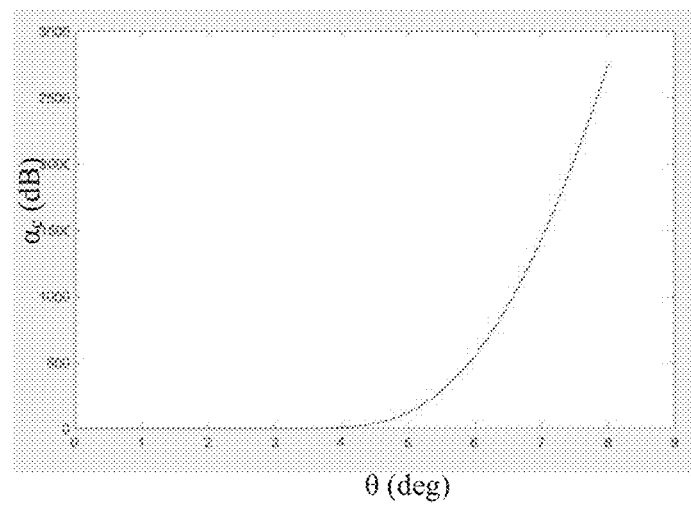
FIG. 3 shows the relationship between the fiber bending loss $\alpha_c$ and $\theta$.

According to the above parameters, if the angle θ of the optical fiber spiral is changed from 0 to 8 degrees, as shown in FIG. 3, the loss will rise sharply at about 4 degrees. By using this great change, light can be scattered from the core wire.

Figure 4:
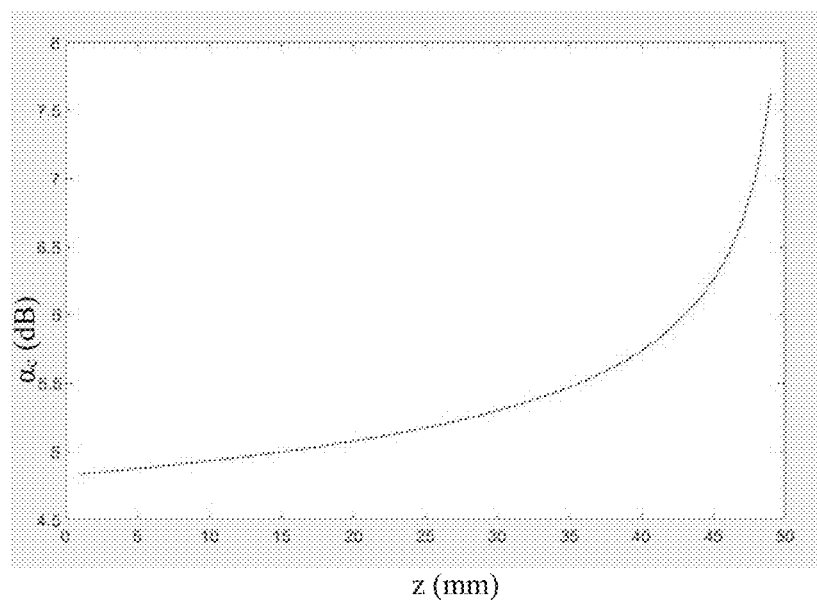
FIG. 4 shows the relationship between $\theta$ and z.

The above parameters are brought into formula (6), and the value of θ corresponding to each z is obtained by a numerical algorithm (for example, a dichotomy or an iterative method), as shown in FIG. 4.

The angle θ of the optical fiber rotation along the axis is set based on the data calculated in FIG. 4, and then a spiral shape of optical fiber with a veritable pitch will be obtained.

According to formula (5), the variation in power can be shown as follows $$P(z) = \frac{s_0}{\frac{\ln(10)}{10}\alpha_c(\theta(z)) \cdot \cos(\theta(z))}$$

Figure 5:
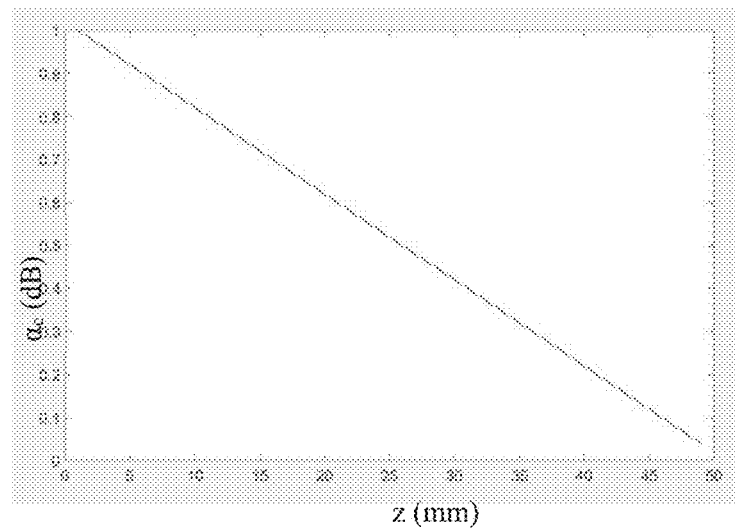
FIG. 5 shows the attenuation of power in optical fiber with z.

When bringing the calculated θ(z) mentioned in the above into this formula, it will obtain the relationship between power and z, as shown in FIG. 5.

From the above, the followings can be known.

1. The bending loss of the transmission power of the optical fiber due to the bending around the metal axis is the optical power of the light exited from the bending side.

The relationship between the bending loss of the single-mode fiber and the bending radius of the optical fiber is calculated according to formula (1):

$$\alpha_c = A_c R^{-1/2} \exp(-UR) \qquad (1);$$

where $$A_c = \frac{1}{2}\left(\frac{\pi}{a}\right)^{1/2} 3.7\left(\frac{\lambda_c}{\lambda}\right)^2 \qquad \text{formula (1)-1}$$

$$U \approx 0.705 \frac{\Delta n^{3/2}}{\lambda}\left(2.748 - 0.996\frac{\lambda}{\lambda_c}\right)^3 \qquad \text{formula (1)-2}$$

In the formula (I), the formula (I)-1, the formula (I)-2, $\alpha_c$ represents the power loss per unit length of the fiber in dB; R represents the bending radius of the optical fiber in mm; $A_c$ represents the parameters related to the optical fiber structure in dB/m½; a represents the radius of core wire of the optical fiber in μm; $\lambda_c$ represents the cutoff wavelength of the fiber transmission in nm; Δn represents the refractive index difference between the core wire and the cladding layer.

In the formula I-1, $$k_0 = \frac{2\pi}{\lambda},$$

$k_0$ is the vacuum wave number, where λ represents the transmission wavelength of the optical fiber;

$$\lambda_c = \frac{2\pi a}{V_c}\sqrt{n_1^2 - n_2^2},$$

where $n_1$ and $n_2$ respectively represent the refractive index of the core wire and cladding layer of the optical fiber; $V_c$ represents the cutoff frequency and $V_c = 2.40483$.

2. The bending radius of the optical fiber is related to the angle between the spiral line of the optical fiber and the side line of the cylinder that is formed by winding the spiral line with radius r, and is calculated according to formula II:

$$R = \frac{4\pi^2 r^2 + (2\pi r \cdot \cot(\theta))^2}{4\pi^2 r};$$

in formula II, R represents the bending radius of the optical fiber, θ represents the angle between the spiral line and the side line of the cylinder, and r represents the spiral winding radius of the optical fiber.

3. The relationship between the longitudinal length of the optical fiber and the angle between the spiral line of the optical fiber and the spiral line of the optical fiber and the side line of the cylinder that is formed by winding the spiral line with radius r is calculated according to formula III:

$$-\frac{\ln(10)}{10}\alpha_c(\theta(z)) \cdot \cos(\theta(z)) \cdot (-s_0 \cdot z + s_1) = -s_0. \qquad \text{formula III}$$

In Formula III, z represents the longitudinal length of the optical fiber along the metal axis, θ represents the angle between the spiral line and the side line of the cylinder; $\alpha_c$ represents the power loss per unit length of the single mode fiber in dB; $s_1$ represents the initial power, $s_0$ represents the rate of power attenuation.

4. When bringing θ(z) obtained from formula III into the following formula IV, the optical power exited from the side of the optical fiber can be calculated:

$$P(z) = \frac{s_0}{\frac{\ln(10)}{10}\alpha_c(\theta(z)) \cdot \cos(\theta(z))} \qquad \text{formula IV}$$

P(z) represents the optical power exited from the side of the optical fiber, i.e., the distribution of the optical power on the longitudinal length of the fiber along the metal axis; z represents the longitudinal length of the fiber along the metal axis; θ represents the angle between the spiral line and the side line of the cylinder; $\alpha_c$ represents the power loss per unit length of a single-mode fiber, in dB.

In the above-mentioned vascular optical fiber guidewire, the pitch of the optical fiber to be set can be calculated by bringing the angle between the spiral line and the side line of the cylinder obtained from formula II or formula III into formula V:

$$h = 2\pi r \cdot \cot(\theta) \qquad \text{Formula V.}$$

In formula V, h represents the pitch of the optical fiber, r represents the spiral winding radius of the optical fiber, and θ represents the angle between the spiral line and the side line of the cylinder. In a specific example, the length of the light-conducting portion of the optical fiber guide wire is 1.6 m. The side-illuminated structure is started at the distance from the top end 50 mm (i.e., the light-emitting portion, the length of z in the formula). The radius r is 200 μm. According to the above formula, the relationship between the angle θ between the spiral line and the side line of the cylinder and z obtained is as shown in FIG. 4. If h and R is known, according to h=2πr·cot(θ), $$R = \frac{4\pi^2 r^2 + (2\pi r \cdot \cot(\theta))^2}{4\pi^2 r}$$

can be calculated.

FIG. 5 shows the power attenuation in the optical fiber 1 caused by the exit of light from the cladding layer, which is due to the gradual decrease of the bending radius of the optical fiber with the variable pitch helical fiber design described above. This indicates that the exit rate of light along z is constant.

Figure 6:
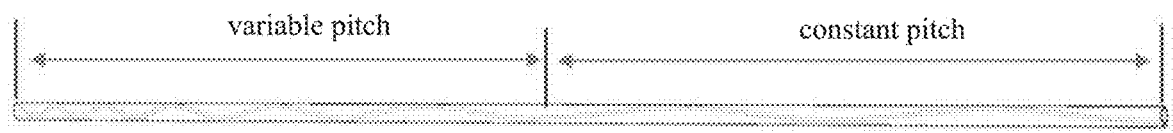
FIG. 6 shows optical fiber guidewires with a constant pitch and a variable pitch.

Further, as shown in FIG. 6, in the main light conducting portion of the optical fiber guide wire, it is not necessary to leak light from the cladding layer, and thus the pitch is set to a value much larger than the critical bending radius Rc; and in the top of the optical fiber guide wire, such as at where from the top 50 mm, the pitch is set to gradually decrease, and the value is changed according to the relationship shown in FIG. 4, and thus light with a constant intensity will scatter from the top along the side face.

Figure 7A:
FIG. 7a is a schematic diagram illustrating the structure of the axial wire.
Figure 7B:
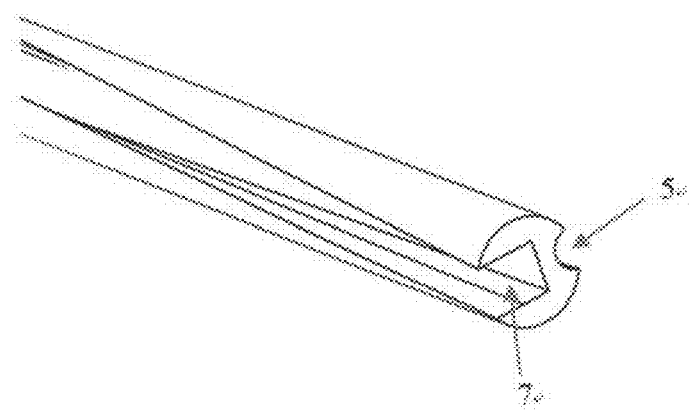
FIG. 7b is a schematic diagram illustrating another structure of the axial wire.
Figure 8:
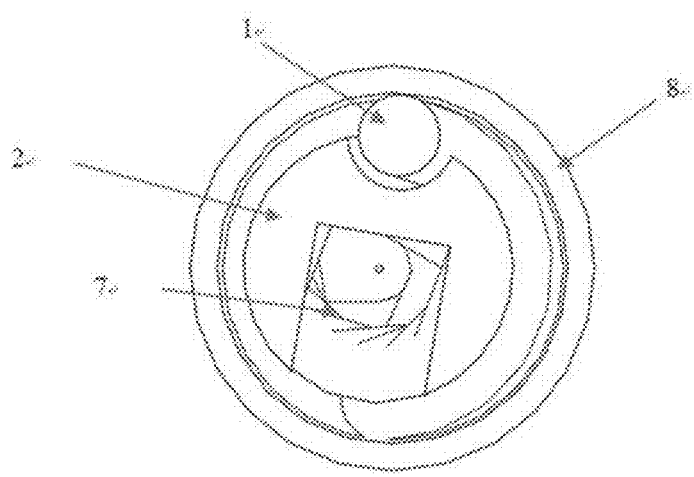
FIG. 8 is a schematic cross-sectional view illustrating an optical fiber guidewire.

Further, the metal axial wire 2 may be a diameter of 50 µm to 1 mm. In order to increase the winding tightness of the optical fiber 1, spiral groove 5 as shown in FIG. 7 may be processed on the metal axial wire 2, so as to embed the optical fiber 1 in spiral groove 5. In order to increase the flexibility of the metal axial wire 2, a hole-like structure (such as, the hole 6) as shown in FIG. 7 may be processed on the side of the metal axial wire 2 to lower the hardness of the metal axial wire 2. It is also possible to process a longitudinal spiral groove 7 as shown in FIG. 7 to lower the hardness of the metal axial wire 2.

Further, a polymer sleeve may be arranged outside the optical fiber guide wire, so as to increase the stability and safety of the overall structure. Moreover, a hydrophilic and/or hydrophobic coating 8 may be arranged outside the polymer sleeve, so as to reduce resistance of the vascular optical fiber guide wire in the blood and increases biocompatibility. A material of the polymer sleeve may be at least one selected from polyethylene, polyvinyl chloride, epoxy resin, aliphatic polyester, chitin and polylactic acid.

The optical fiber 1 of the present disclosure may be a quartz optical fiber, a polymer optical fiber or a glass optical fiber. A material of the cladding layer may also be quartz or the like, as long as the refractive index is lower than that of the optical fiber, so that light can be transmitted only in the optical fiber without being exited from the cladding layer.

Material of the metal axial wire 2 of the present disclosure may be stainless steel, aluminum alloy, titanium alloy or nickel titanium alloy, and may also be carbon fiber, polymer material or the like. The polymer material used is at least one selected from polyethylene, polyvinyl chloride, epoxy resin, aliphatic polyester, chitin and polylactic acid.

Example 3

On the basis of example 1 or 2, one end of the light-conducting portion 21 (i.e., the end left outside the body) is connected with a memory apply plug 22. Due to the arrangement of the memory metal plug 22, the vascular fiber guide wire can be connected with other optical fiber to achieve the extension, or the vascular fiber guide wire can be connected to a laser to introduce conveniently laser into light-conducting portion 21.

Figure 9:
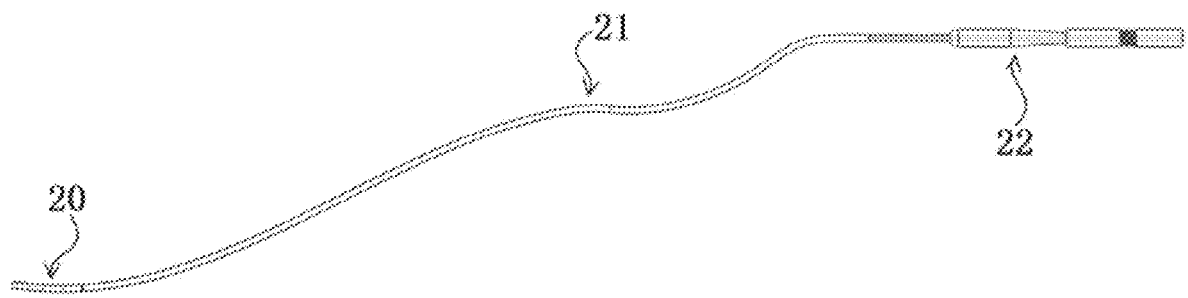
FIG. 9 is a schematic diagram illustrating the structure of a vascular optical fiber guidewire with a memory alloy plug according to the present disclosure.

As shown in FIG. 9, it is a schematic diagram illustrating the structure of a vascular optical fiber guidewire with a memory alloy plug according to the present disclosure. The light conducting portion 21 has one end connected to the light emitting portion 20 and the other end connected to the memory alloy plug 22, and the overall shape thereof may be cylindrical or cylindrical-like.

Figure 10:
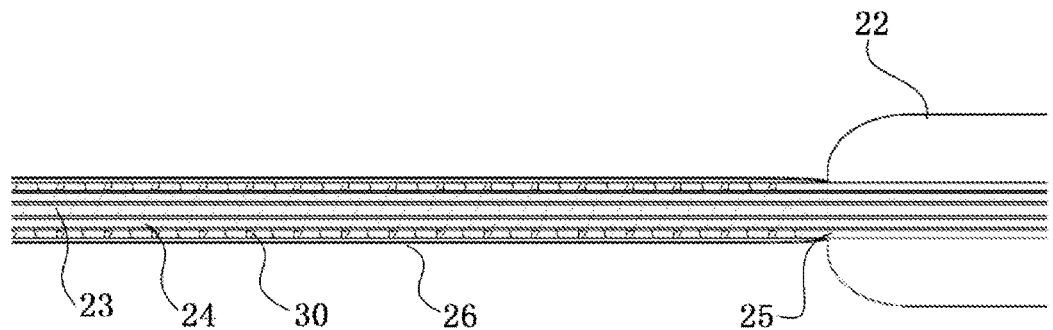
FIG. 10 is a schematic diagram illustrating the structure of the vascular optical fiber guidewire of FIG. 9.

The structure of the light-conducting portion 21 is as shown in FIG. 10, and the memory alloy plug 12 is as shown in FIG. The light conducting portion 21 includes a conducting portion fiber 210 that includes an optical fiber core 23 and a fiber cladding 24.

Figure 11:
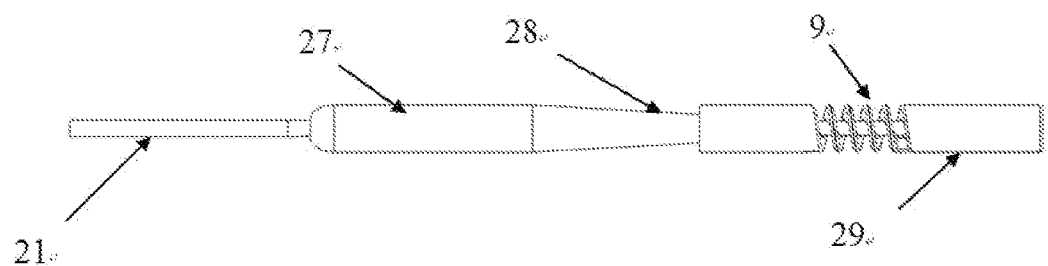
FIG. 11 is a schematic diagram illustrating the structure of the memory alloy plug of FIG. 9.

The structure of the optical fiber guidewire 21 is as shown in FIG. 10, and the memory alloy plug 12 is as shown in FIG. 11. The light conducting portion 21 includes a conducting optical fiber 210, and the conducting optical fiber 210 includes optical core wire 23 and an optical fiber cladding layer 24.

The memory alloy plug 22 is composed of a handle 27, a fixing groove 28, and a sleeve 29. The handle 27 is a hand-held operating portion. A radius of an end of the fixing groove 28 connected to the handle 27 is larger than a radius of an end of the fixing groove 28 connected to the sleeve 29. That is, the fixing groove 28 is a truncated cone structure with the outer diameter being gradually decreasing from one end (i.e., the end connected with the handle 27) to the other end (i.e., the one end connected with the sleeve 29). Specifically, the end connected to the handle 27 has a large diameter, and the end connected to the sleeve 29 has a small diameter. The fixing groove 28 is used for mating with an external connector, so as to provide locking effect. The sleeve 29 is provided with an elastically deformable spiral structure 9 and the elastic deformable spiral structure 9 can be disposed at an intermediate position of the sleeve 29. That is, the sleeve 29 is divided into two parts by the elastic deformable spiral structure 9 which is just located between the two parts. The elastic deformable spiral structure 9 is composed of a plurality of spiral coils and made by spirally cutting a memory alloy material, such as a nickel-titanium alloy or a copper-zinc alloy. The serial structure by using the memory alloy has high deformability, and can be used repeatedly.

Figure 12:
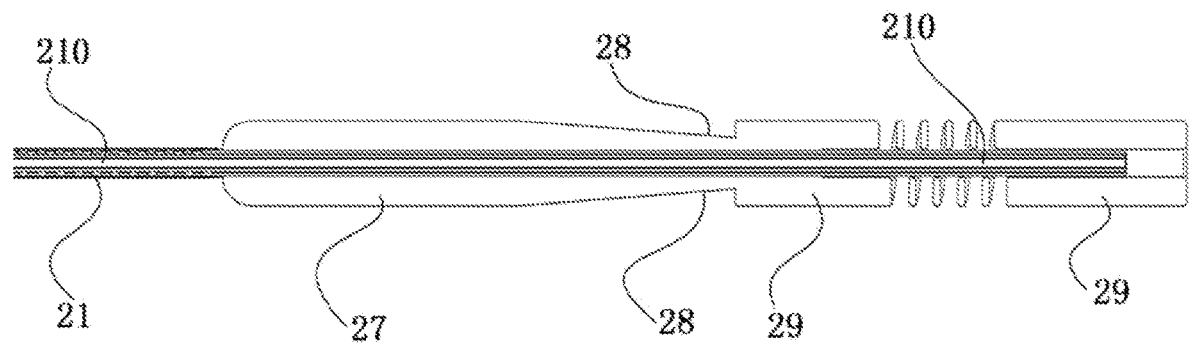
FIG. 12 is a cross-sectional diagram of the memory alloy plug of FIG. 9.

The conducting optical fiber 210 extends through the memory metal plug 22. In other word, the memory metal plug 22 wraps around the conducting optical fiber 210, as shown in FIG. 12. It is preferred that a small gap is provided between the conducting optical fiber 210 or the light conducting portion 21 and the sleeve 29. When the sleeve 29 is extended or contracted due to force, the sleeve 29 will slide longitudinally along the light conducting portion 21 or the conducting optical fiber.

Figure 13:
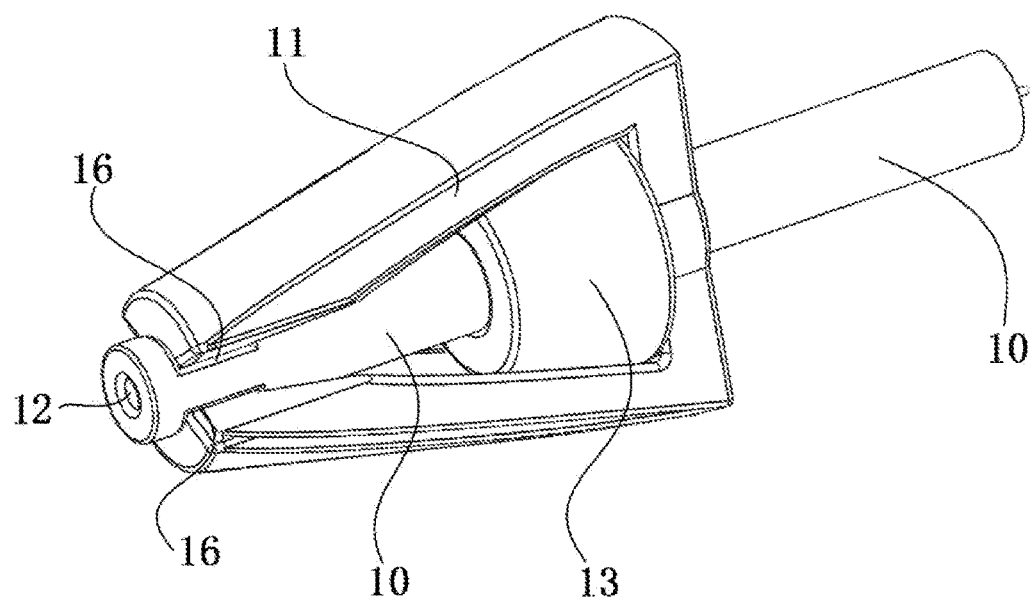
FIG. 13 is a schematic diagram illustrating a structure of jack set.

The memory alloy plug 22 can be inserted into the jack set (as shown in FIG. 13). The jack set includes the main body 10. Along an axial direction of the main body 10, a connecting optical fiber 14 is arranged at an axial center inside one end of the main body 10, and a cavity 12 capable of accommodating the memory metal plug 22 is arranged at an axial center inside other end of the main body 10, so that when the memory alloy plug 22 is inserted into the cavity, the conducting optical fiber wrapped at the axial central of the memory alloy plug 22 is exactly paired with the connecting optical fiber 14, and the conducting optical fiber is brought into contact with or close to the connecting fiber 14. Therefore, light can be transmitted from the connecting fiber 14 to the conducting optical fiber with high transmission efficiency. An elastic pin 11 is sleeved on the main body 10. When the memory alloy plug 22 is inserted into the cavity 12 of the main body 10, the elastic pin 11 can be snapped into the fixing groove 28, so as to be fixed to the memory metal plug 22.

Figure 14:
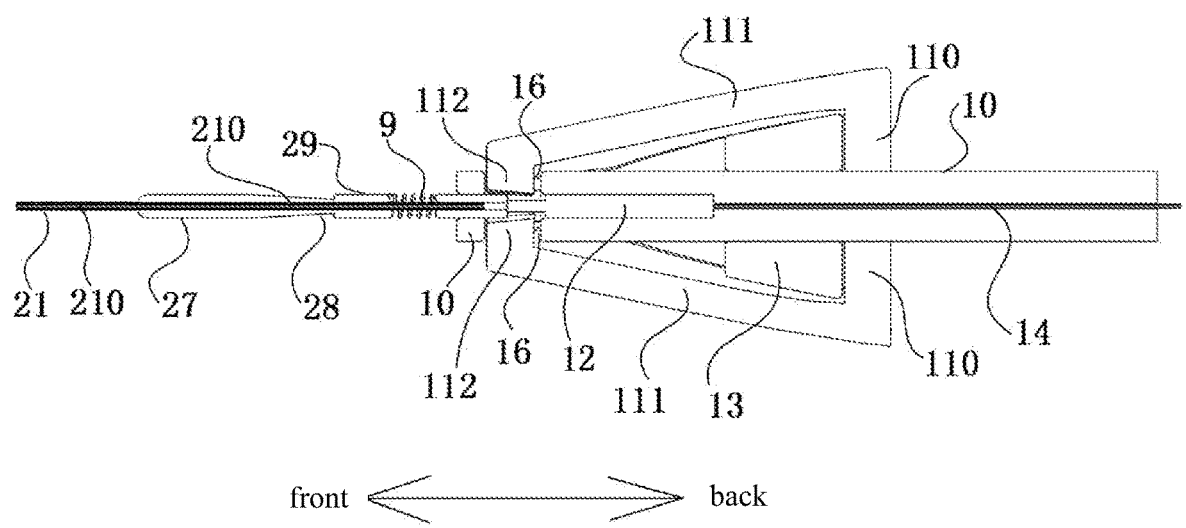
FIG. 14 is a cross-sectional diagram illustrating the structure that the memory alloy plug is inserting into the jack set.
Figure 15:
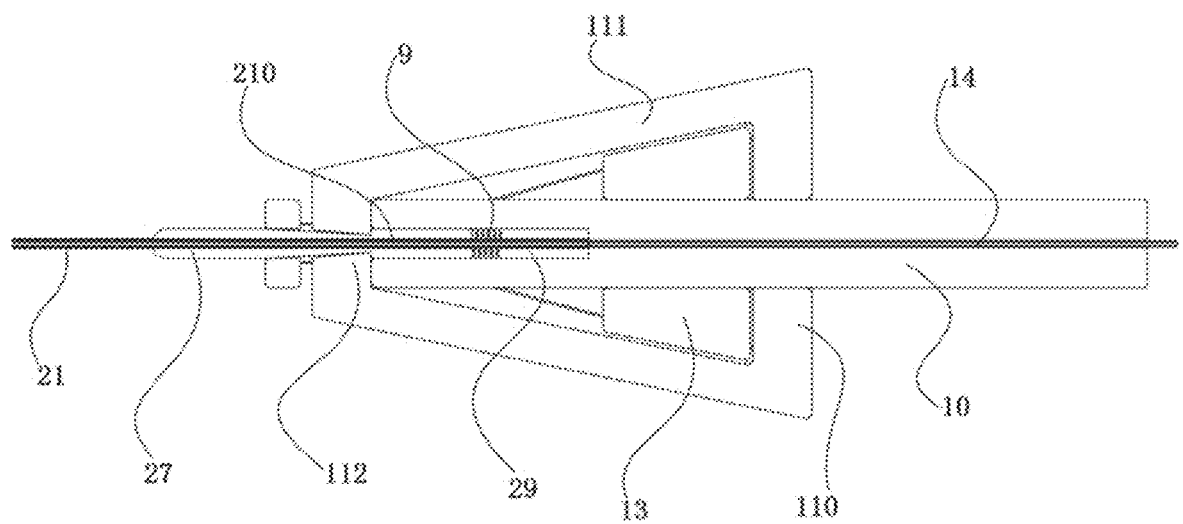
FIG. 15 is a cross-sectional diagram illustrating the structure that the memory alloy plug has been inserted into the jack set.

Referring to FIGS. 13-15, the elastic pin 11 includes a connecting portion 110 that can be connected to the main body 10. Both ends of the connecting portion 110 are symmetrically connected with an elastic portion 111. Ends of two elastic portions 111 are respectively provided with a fixing portion 112 inwardly. Fixing portions 112 are parallel to the connecting portion 110. Each of the two elastic portions 111 is gradually inclined inward from a back end (i.e., the end connected to the connecting portion) to a front end (i.e., the end connected to the fixing portion), so that the elastic pin 11 has a small diameter at the end of the fixing portion and a large diameter at the end of the connecting portion 110. The main body 10 enters the elastic pin from the connecting portion 110 and passes between the two fixing portions 112 at the end having the small diameter of the elastic pin. In addition, the main body 10 of the elastic pin is sleeved with a rolling ring 13. The rolling ring 13 can roll or slide along the main body 10. And the rolling ring 13 moves on the main body 10 to deform the elastic pin 11, so as to insert or release the memory alloy plug 22.

As shown in FIG. 13-15, two opposite sides of the main body 10 are provided with openings 16 penetrating through a wall of the cavity. Two openings 16 are respectively disposed corresponding to the two fixing portions 112. In the natural state of the elastic pin (when the elastic pin is closed), the two fixing portions 112 are respectively located at the openings 16 on both sides of the main body 10, and the rolling ring 13 is located at the end with the large diameter of the elastic pin. An outer diameter of the rolling ring 13 is the same as the inner diameter of the end with the large diameter of the elastic pin 11. Since the elastic pin 11 possesses a flat tapered structure or a flat truncated cone structure, the inner diameter thereof is also reduced from the front end to the back end. Therefore, when the rolling ring 13 is moved toward the end with small diameter of the elastic pin (i.e., the direction toward the fixing portion 112), the periphery of the rolling ring 13 gradually will apply an outward force to the elastic portion 111, so that the elastic portion 111 is opened and the fixing portion 112 comes out from the opening 16; when the rolling ring 13 is moved toward the back end, the force against the elastic portion 111 will disappear, so that the elastic portion 111 rebounds to the original position and the fixing portion 112 returns to the opening 16, i.e., the elastic pin 11 is closed.

Preferably, the end face of the fixing portion 112 is an inclined face that can be matched with the end face of the fixing groove 28. In other word, the inclined face is inclined inward from the front end to the back end, forming a structure having a large diameter at the front end and a small diameter at the back end. When the sleeve 29 of the memory metal plug 22 is inserted into the cavity 12, the inclined surfaces (i.e., the end face) of the two fixing portions 112 are exactly located in the fixing groove 28, so that the cooperation therebetween is safely and securely.

As shown in FIGS. 14-15, the main body 10 has a connecting optical fiber 14 at the axial central. When the memory alloy plug 22 is inserted into the cavity 12 of the jack set, the sleeve 29 will lift the fixing portion up at the opening 16 when passing through the opening 16, while the lift-up of fixing portion 112 will spring the elastic portion 111. That is, the elastic pin 11 is opened under the pushing of the sleeve 29, and the sleeve 29 of the memory alloy plug 22 enters the insertion hole 12. When the memory alloy plug 22 is inserted to the depth of the full-filled socket, the pitches of the elastic deformable spiral structure 9 of the memory alloy plug 22 contracts due to force, the fixing groove 28 is exactly located at the opening 16, and the fixing portion 112 is exactly snapped into the fixing groove 28, so that the elastic pin 11 is snapped by the fixing groove 28 of the memory metal plug 22 and the conducting optical fiber inside the optical fiber guidewire is docked with the connecting fiber 14 of the jack set to realize coupling. The inclined face of the fixing portion 112 is inclined inward from the front end to the back end, which also facilitates the sleeve 29 to smoothly pass through the opening and to lift the fixing portion 112 up.

As shown in FIG. 15, the connecting optical fiber 14 can be connected to the laser. In use, the light-emitted portion of optical fiber guidewire enters the body and reaches affected sites including the liver tumor tissue through blood vessels; then laser is emitted from the laser, then is transmitted to the conducting optical fiber through the connecting optical fiber 14, and then is transmitted from an end of the conducting optical fiber to the optical fiber of the light-emitted portion. Light then reaches the affected sites of human body by the optical fiber of the light-emitted portion, so as to achieve the required treatment. When the treatment with laser is completed, the laser is turned off. The rolling ring 13 is pushed toward the fixing portion 112 to force the elastic pin 11 opening, so that the memory alloy plug 22 is sprang from the cavity 12 under the elastic deformation spiral force. In this example, compared with a common metal plug, the memory alloy plug of the disclosure has greater elastic deformability and can be used repeatedly without changing the accuracy. Moreover, the matching structure of the spiral and the elastic pin in the elastic deformable spiral structure 9 has such a flexibility to ensure the proper matching of the optical fiber, and does not break due to fatigue during multiple using. This example brings out good comprehensive effects.

Preferably, a metal tube 25 is provided at the center of the memory alloy plug 22. The metal tube 25 extends in the direction of the light-conducting portion and is wrapped around the periphery of the conducting optical fiber. The spiral tube 30 is located at the periphery of the optical fiber wires and formed by spirally cutting metal tube, and thus can be used for supporting or protecting the light-conducting portion 21. A polymer coating 26 is provided outside the spiral tube 30, which increases the lubricity and biocompatibility of the light-conducting portion 21 and reduces the resistance in the blood.

It should be noted that the metal tube 25 can wrap around all of optical fibers (or the light-conducting portion 21) penetrated inside the memory metal plug. In this situation, a small gap is provided between the sleeve 29 and the metal tube 25, so that when the sleeve 29 is contracted due to force, the sleeve 29 can slide along the metal tube 25.

In this example, the vascular fiber guide wire is connected to the laser or other optical fiber and other equipment through the memory alloy plug in which the plug is convenient to insert/remove into/from the jack set. In addition, the optical fiber is rotatable after inserting the plug, so the coupling efficiency would not be affected. The metal tube is spirally cut to form a spiral tube to protect and support the conducting optical fiber.

In the present disclosure, the terms "conducting optical fiber 210", "optical fiber 1", "connecting optical fiber 14" and the like are named differently, but they have the same structure including the cross-sectional structure, and include a core for transmitting light and a cladding layer for restraining the transmission of light.

In the present disclosure, the bending radius R and the critical bending radius Rc are both concepts in the prior art. Rc belongs to or is included in R, and Rc is a special value in R. The bending radius is the radius of curvature. Broadly speaking, when a small segment of the curve is replaced by a circular arc, the radius of the circular arc is the radius of curvature. It is generally understood that the critical bending radius Rc of the present disclosure is the minimum bending radius at which the cladding layer can just constraining the light transmitted in the core wire, resulting in light not to leak out from the sidewall, and light is leaked out from the sidewall as long as R is less than this radius.

The above description are only preferred embodiments of the present disclosure. It should be appreciated that various modifications and changes can be made to the present disclosure. Any modifications, equivalents, improvements, etc., made within the spirit and the scope of the present disclosure are intended to be included within the scope of the present disclosure.

The invention claimed is:

1. A side-illuminated vascular optical fiber guidewire, comprising
   a light-conducting portion, wherein one end of the light-conducting portion is connected to a light-emitting portion;
the light-emitting portion comprises a metal axial wire and an optical fiber surrounding the metal axial wire;
the optical fiber comprises a core wire and a cladding layer covering the core wire; and
in the light-emitting portion, when a bending radius of the optical fiber around the metal axial wire is less than a critical bending radius, a light in the core wire may be scattered from a sidewall to achieve lighting.

2. A side-illuminated vascular optical fiber guidewire, comprising a light-conducting portion, wherein:
one end of the light-conducting portion is connected to a light-emitting portion;
the light-emitting portion comprises a metal axial wire and an optical fiber surrounding the metal axial wire;
the optical fiber comprises a core wire and a cladding layer covering the core wire;
a diameter of the metal axial wire is 50 μm to 1 mm; and
a spiral groove is on the metal axial wire.

3. The vascular optical fiber guidewire according to claim 1, wherein a bending loss of transmission power of the optical fiber due to a bending around the metal axial wire is an optical power of light exited from a bending side face;
a relationship between the bending loss of a single-mode fiber and the bending radius of the optical fiber is calculated according to formula I:

$$\alpha_c = A_c R^{-1/2} \exp(-UR) \qquad \text{formula I;}$$

wherein $$A_c = \frac{1}{2}\left(\frac{\pi}{a}\right)^{1/2} 3.7 \left(\frac{\lambda_c}{\lambda}\right)^2 \qquad \text{formula I-1}$$

$$U \approx 0.705 \frac{\Delta n^{3/2}}{\lambda}\left(2.748 - 0.996 \frac{\lambda}{\lambda_c}\right)^3 \qquad \text{formula I-2}$$

in the formula I, the formula I-1, the formula I-2, $\alpha_c$ represents the power loss per unit length of the optical fiber in dB; R represents the bending radius of the optical fiber in mm; $A_c$ represents parameters related to structure of the optical fiber in dB/m½; a represents the radius of the core wire of the optical fiber in μm; $\lambda_c$ represents the cutoff wavelength of transmission of the optical fiber in nm; Δn represents the refractive index difference between the core wire and the cladding layer; and
in the formula I-1, $$k_0 = \frac{2\pi}{\lambda},$$

$k_0$ is the vacuum wave number, where λ represents the transmission wavelength of the optical fiber;

$$\lambda_c = \frac{2\pi a}{V_c}\sqrt{n_1^2 - n_2^2},$$

where $n_1$ and $n_2$ respectively represent the refractive index of the core wire and the refractive index of the cladding layer of the optical fiber; $V_c$ represents the cutoff frequency, and $V_c = 2.40483$.

4. The vascular optical fiber guidewire according to claim 3, wherein the bending radius of the optical fiber is related to an angle between a spiral line of the optical fiber and a side line of a cylinder that is formed by winding the spiral line with radius r, which is calculated according to formula II:

$$R = \frac{4\pi^2 r^2 + (2\pi r \cdot \cot(\theta))^2}{4\pi^2 r}; \qquad \text{formula II}$$

in formula II, R represents the bending radius of the optical fiber, θ represents the angle between the spiral line and the side line of the cylinder, and r represents the winding radius of the spiral line of the optical fiber;
a relationship between a longitudinal length of the optical fiber and the angle between the spiral line of the optical fiber and the side line of the cylinder that is formed by winding the spiral line with radius r is calculated according to formula III $$-\frac{\ln(10)}{10}\alpha_c(\theta(z))\cdot\cos(\theta(z))\cdot(-s_0\cdot z + s_1) = -s_0; \qquad \text{formula III}$$

and
in formula III, z represents the longitudinal length of the optical fiber along the metal axis, θ represents the angle between the spiral line and the side line of the cylinder; $\alpha_c$ represents the power loss per unit length of the single-mode fiber in dB; $s_1$ represents the initial power, $s_0$ represents the rate of power attenuation.

5. The vascular optical fiber guidewire according to claim 4, wherein when bringing θ(z) obtained from formula III into following formula IV, an optical power exited from the side face of the optical fiber is obtained:

$$P(z) = \frac{s_0}{\frac{\ln(10)}{10}\alpha_c(\theta(z))\cdot\cos(\theta(z))} \qquad \text{formula IV}$$

wherein P(z) represents the optical power exited from the side face of the optical fiber, i.e., a distribution of the excited optical power on the longitudinal length of the optical fiber along the metal axis; z represents the longitudinal length of the optical fiber along the metal axis; θ represents the angle between the spiral line and the side line of the cylinder; $\alpha_c$ represents the power loss per unit length of the single-mode fiber in dB.

6. The vascular optical fiber guidewire according to claim 5, wherein a pitch of the optical fiber to be set is calculated by bringing the angle between the spiral line and the side line of the cylinder obtained from formula II or formula III into formula V:

$$h = 2\pi r \cot(\theta) \qquad \text{Formula V}$$

wherein in formula V, h represents the pitch of the optical fiber, r represents a winding radius of the spiral line of the optical fiber, and θ represents the angle between the spiral line and the side line of the cylinder.

7. The vascular optical fiber guidewire according to claim 4, wherein a pitch of the optical fiber to be set is calculated by bringing the angle between the spiral line and the side line of the cylinder obtained from formula II or formula III into formula V:

$$h = 2\pi r \cdot \cot(\theta) \qquad \text{Formula V}$$

and wherein in formula V, h represents the pitch of the optical fiber, r represents a winding radius of the spiral line of the optical fiber, and θ represents the angle between the spiral line and the side line of the cylinder.

8. The vascular optical fiber guidewire according to claim 1, wherein a diameter of the metal axial wire is 50 μm to 1 mm; and a spiral groove is on the metal axial wire.

9. The vascular optical fiber guidewire according to claim 1, wherein a hole-like structure is on the metal axial wire; and a polymer sleeve is outside the optical fiber guidewire.

10. The vascular optical fiber guidewire according to claim 1, wherein another end of the light-conducting portion is connected with a plug capable of connecting with a laser or other optical fiber.

11. The vascular optical fiber guidewire according to claim 2, wherein in the light-emitting portion, when a bending radius of the optical fiber around the metal axial wire is less than a critical bending radius, a light in the core wire may be scattered from a sidewall to achieve lighting.

12. The vascular optical fiber guidewire according to claim 11, further comprising:
a hole-like structure on the metal axial wire; and
a polymer sleeve outside the optical fiber guidewire.

13. A side-illuminated vascular optical fiber guidewire, comprising a light-conducting portion, wherein:
one end of the light-conducting portion is connected to a light-emitting portion;
the light-emitting portion comprises a metal axial wire and an optical fiber surrounding the metal axial wire;
the optical fiber comprises a core wire and a cladding layer covering the core wire;
a hole-like structure is on the metal axial wire; and
a polymer sleeve is outside the optical fiber guidewire.

14. The vascular optical fiber guidewire according to claim 13, wherein the metal axial wire has a longitudinal spiral groove on a side opposite to the spiral groove; and a hydrophilic and/or hydrophobic coating is outside the polymer sleeve.

15. The vascular optical fiber guidewire according to claim 13, wherein in the light-emitting portion, when a bending radius of the optical fiber around the metal axial wire is less than a critical bending radius, a light in the core wire is scattered from a sidewall to achieve lighting.

16. The vascular optical fiber guidewire according to claim 13, wherein another end of the light-conducting portion is connected with a plug capable of connecting with a laser or other optical fiber.

17. A side-illuminated vascular optical fiber guidewire, comprising
a light-conducting portion,
wherein one end of the light-conducting portion is connected to a light-emitting portion;
the light-emitting portion comprises a metal axial wire and an optical fiber surrounding the metal axial wire;
the optical fiber comprises a core wire and a cladding layer covering the core wire; and
another end of the light-conducting portion is connected with a plug capable of connecting with a laser or other optical fiber.

18. The vascular optical fiber guidewire according to claim 17, wherein in the light-emitting portion, when a bending radius of the optical fiber around the metal axial wire is less than a critical bending radius, a light in the core wire is scattered from a sidewall to achieve lighting.

19. The vascular optical fiber guidewire according to claim 17, further comprising a hole-like structure on the metal axial wire.

20. The vascular optical fiber guidewire according to claim 17, further comprising a polymer sleeve outside the cladding layer.

* * * * *